United States Patent [19]

Wood

[11] Patent Number: 4,895,164

[45] Date of Patent: Jan. 23, 1990

[54] INFRARED CLINICAL THERMOMETER

[75] Inventor: Don E. Wood, Irvine, Calif.

[73] Assignees: Telatemp Corp., Fullerton; Temp-Stik Corporation, San Juan Capistrano, both of Calif.

[21] Appl. No.: 244,738

[22] Filed: Sep. 15, 1988

[51] Int. Cl.[4] ............................ A61B 5/00; G01J 5/00; G01K 1/08

[52] U.S. Cl. .................................... 128/736; 374/124; 374/126; 374/164

[58] Field of Search ................. 374/141, 129, 124, 33; 128/644, 736

[56] References Cited

U.S. PATENT DOCUMENTS

| | | | |
|---|---|---|---|
| 3,491,596 | 1/1970 | Dean | 128/736 X |
| 3,492,058 | 1/1970 | Waldman | 250/353 X |
| 3,581,570 | 1/1971 | Wortz | 128/736 |
| 3,718,437 | 2/1973 | Paloniemi | 374/33 X |
| 4,602,642 | 7/1986 | O'Hara et al. | 128/644 |
| 4,634,294 | 1/1987 | Christol et al. | 374/129 X |
| 4,636,091 | 1/1987 | Pompei et al. | 374/124 |

FOREIGN PATENT DOCUMENTS 2836462 3/1980 Fed. Rep. of Germany ...... 340/600

OTHER PUBLICATIONS

Tympanic Clinical Temperature, M. Benzinger et al., Jun. 21-24, 1971, presented at Fifth Symposium on Temperature, Washington, D.C.

Primary Examiner—Daniel M. Yasich
Attorney, Agent, or Firm—Hopgood, Calimafde, Kalil, Blaustein & Judlowe

[57] ABSTRACT

A clinical infrared thermometer is disclosed for use in measuring the internal temperature of living subjects. The system operates by the combination of a radiation sensor that is held in isothermic condition with wave guide at ambient temperature. A thermistor, or other temperature sensor, is thermally coupled thereto and compensates for changes in ambient conditions.

21 Claims, 3 Drawing Sheets

INFRARED CLINICAL THERMOMETER

BACKGROUND OF THE INVENTION

The present invention is generally related to temperature measuring devices, and more particularly, to an apparatus for measuring temperature by collecting infrared radiation from a target and converting the infrared radiation into a signal proportional to the target temperature. In one embodiment, the present invention operates as a clinical thermometer for the measurement of human body temperature.

It has long been the interest of medical professionals to measure and monitor the body temperature of their patients. This interest is primarily based on the fundamental relationship existing between the pathologic state and internal body temperature. Many illnesses are characterized by a deviation from normal body temperature, and the success of certain medical regimens, e.g., antibiotics, is best tracked by directly monitoring the body temperature and its response to the regimen.

In the past, mercury thermometers have been predominantly relied upon for the measurement of body temperature. Although the mercury thermometer has enjoyed universal use, it suffers from several key drawbacks. The mercury thermometer as a contact sensor, takes several minutes to equilibrate in temperature with the contacted tissue. This equilibration time is a significant cost factor when patients number in the hundreds as in hospital wards. Also, the contacted tissue may be and often is a source of infectious bacteria and viral agents, thus necessitating additional time for sterilization of the thermometer between readings. In addition, mercury thermometers are most often contacted to mucous membranes in the mouth or rectum; both locations have been found to be less than perfect predictors of the internal body temperature of the patient.

Electronic thermometers using a permanent thermistor probe with a disposable probe cover have replaced many of the glass thermometers, especially in hospitals. Those thermometers have the advantage over glass thermometers in that they give a reading in about 40 seconds and in that the reading is digital. But, in 40 seconds thermal equilibrium has not yet been reached with the thermistor thermometers generally used. The thermometer electronics provides a correction by interpolating the time-temperature curve to "predict" an estimated stabilized reading. This technique introduces errors and makes accuracy verification against a temperature standard difficult or impossible.

Some of the above problems have been alleviated by the use of thermocouple probes, which now can be made to be both disposable and characterized by a relatively short time constant. Still the thermocouple probe remains a device designed to contact the patient's mucous membranes with both the remote possibility of cross-contamination and less than ideal accuracy.

In the search for a better thermometer, it has become known that the tympanic membrane or the ear drum is characterized by an inherent temperature that is essentially identical to the internal temperature of the body. The tympanic membrane is both delicate (i.e., easily damaged) and sensitive, therefore making the application of a contact-type sensor to the tympanic membrane less attractive.

Non-contact sensing of temperature becomes possible through the application of infrared radiation sensor technology. Infrared radiation sensors such as the thermopile type, have found substantial use for temperature measurement of remote or environmentally isolated targets. For example, the temperature of stars, planets, and furnaces are all measured by sensing the emitted infrared radiation from the target surface. In these applications, the infrared radiation sensors have been found to have high accuracies within narrow temperature ranges. Accurate measurements within 0.1 degrees Fahrenheit have been attained.

The use of an infrared radiation sensor to measure the temperature of the tympanic membrane has been attempted. For example, U.S. Pat. No. 4,602,642, discloses a temperature sensor based on infrared radiation detection. This instrument is based on a design that is quite complicated. For example, a complex sensor heating apparatus is operated with a close loop temperature controller to hold the temperature of the thermopile detector constant near the patient's body temperature, i.e., 98.6° Farenheit. In addition, the device requires frequent calibration, based on a microprocessor controlled calibration sequence, against a target heated to a controlled temperature. Also, the use of the instrument requires considerable training and skill, since it has to be very carefully pointed toward the tympanic membrane in order to give an accurate temperature read out. These complexities have made the device difficult and expensive to manufacture and unaffordable to the majority of users.

It was with this understanding of the problems associated with the prior art that the subject invention was made.

OBJECTS AND SUMMARY OF THE INVENTION

Accordingly, it is the primary object of the present invention to provide a sensor device capable of measuring temperature based on infrared radiation as emitted from a target.

It is another object of the present invention to measure temperature of the tympanic membrane in a human ear by collecting infrared radiation from the tympanic membrane and converting the collected radiation into a temperature dependant output signal.

Yet another object of the present invention is to accurately determine temperature based on infrared radiation, using an isothermal detector assembly operating at ambient temperature.

A further object of the present invention is to provide a temperature measuring system that is easily used requiring relatively unskilled operators and relatively inexpensive to manufacture.

The above objects are realized in an infrared clinical thermometer apparatus and system comprising a housing with an infrared radiation receiving port at one end. Contained in the housing is an infrared radiation sensor assembly which further comprises a wave guide, thermopile sensor, thermistor, and heat conducting block. The infrared radiation sensor assembly is constructed and configured so as to remain in an isothermic state, even during changes of ambient temperature. Further, the infrared radiation sensor assembly is positioned within the housing so as to form an insulative airspace between the housing wall and the isothermic assembly. The wave guide extends through the housing via the infrared radiation receiving port. In addition, the housing contains a power source and signal processing board. Control switches and a temperature display are disposed on the external surface of the housing, which is generally shaped to conform to the operator's hand. The housing is also shaped in such a way that the operator will automatically point the instrument toward the tympanic membrane by leaning the hand holding the instrument against the cheek of the patient (a procedure taught as mandatory in the use of otoscopes).

In operation, a disposable speculum is placed over that portion of the wave guide that extends outside of the housing. The speculum, which is transparent to the infrared radiation at the chosen frequency, is then placed into the patient's ear. Infrared radiation, emitted from the tympanic membrane in the ear and tissue adjacent to the tympanic membrane, travels down the wave guide and impinges the infrared radiation detector which produces a signal corresponding thereto. The thermistor or other temperature sensor concurrently measures the temperature of the isothermic assembly. These signals form the input to the signal processor which generates the measured temperature, which, in turn, is displayed.

DETAILED DESCRIPTION OF THE PREFERRED EMBODIMENT

Figure 1:
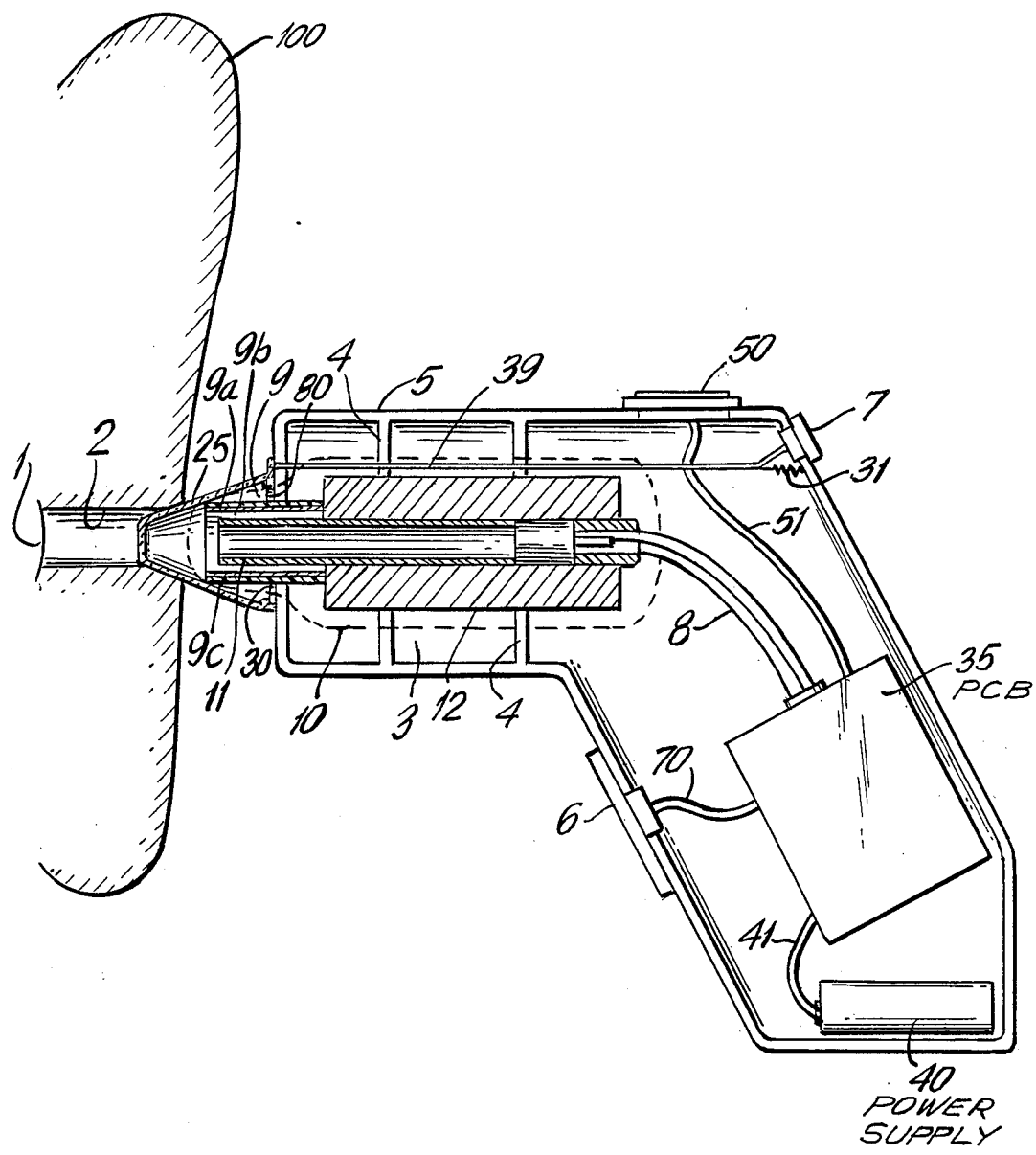
FIG. 1 is a longitudinal cross-section view of the temperature sensing device of the present invention, indicating the various components therein, and its relationship to a patient's ear.

Referring now to FIG. 1, a detailed cross-section view of the inner components of subject invention is presented. In this context, the apparatus is shown in relationship to a patient's ear 100. More specifically, ear 100 is shown with ear canal 2, terminating with ear drum 1. The ear drum is characterized by a tympanic membrane generally disposed outward and down ear canal 2. This tympanic membrane emits infrared radiation in proportion to its temperature; infrared radiation travels down the ear canal and becomes available for collection at the ear opening.

The temperature measuring apparatus as presented in FIG. 1 has housing 5 which provides an enclosure of the working elements of the device. Housing 5 can be made of any material suitable for containing electronic components, but is preferably constructed in a lightweight rigid plastic material. Plastic is preferred for its relatively high strength/weight ratio, ease in manufacturing through injection molding techniques, low thermal conductivity, and for the relatively inexpensive material costs associated with most plastics. It may be that more demanding uses and environments will require other materials such as composites or fiberglass for housing 5, but for most applications, plastics such as polyethylene and polypropylene should suffice.

Integral with Housing 5, are spacer studs 4 that extend radially inwards from the housing wall. These spacer studs, preferably made of material of low thermal conductivity such as nylon, structurally support the infrared radiation sensor assembly which is designated by the numeral 10, within airspace 3 in housing 5. In this regard, airspace 3 provides an insulative layer of air that surrounds infrared radiation sensor assembly 10 and minimizes the heat transfer from heat sources external to housing 5 to the infrared radiation sensor assembly.

Figure 2:
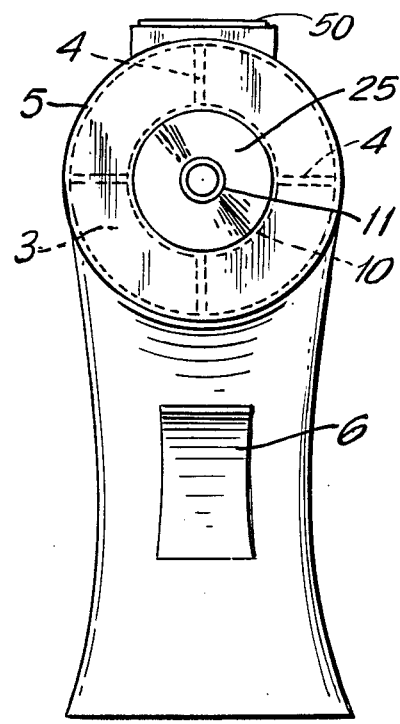
FIG. 2 is a frontal view of the apparatus of the present invention, where the insulating airspace is shown between the housing and sensor assembly.

Now referring to FIG. 2, airspace 3 can be seen as the annular region between the housing wall and the infrared radiation sensor assembly 10. The broken lines in FIG. 2 represent spacer studs 4 retaining the annular position of the infrared radiation sensor assembly 10. For most of the applications, airspace 3 will provide a sufficient insulative barrier between the housing wall and the infrared radiation sensor assembly. It may be that other insulative means can be substituted for the more demanding applications. These can include freon-filled foamed polymers, vacuum gap, or similar. The extra cost associated with such insulative means must, of course, be justified by the need for a lower heat transfer rate or smaller dimensioned housing. The distance between the housing wall and infrared radiation assembly 10 is not particularly limitative, and can range between 5 and 50 mm.

Referring back to FIG. 1, a second airspace is formed by speculum 25 and wave guide 11 and is designated by the number 9. Airspace 9 acts to insulate wave guide 11 from heat sources external to speculum 25. In order to further prevent heating of the protruding portion of the proximal end of the wave guide, especially while inserting a speculum, a low emissivity barrier 9a, such as polished or gold plated aluminum tubing, is placed around the protruding portion of the wave guide. In addition, air space 9b and a plastic low thermal conductivity covering, 9c over tubing 9a, provides further thermal protection for the protruding portion of the wave guide.

Printed Circuit Board ("PCB") designated as 35 in FIG. 1 is positioned within housing 5. The PCB provides the signal processing for the apparatus. More particularly, PCB 35 receives a signal from infrared radiation sensor assembly 10, via cable 8. This signal is amplified and converted via the circuitry on PCB 35 by means well known in the electronics art, i.e., the input signal is amplified sufficiently to drive the display 50, and also converted to reflect the temperature units for the system (i.e., Fahrenheit or Celsius). The PCB is powered by power supply 40 via cable 41. The power supply is preferably a long life 9-Volt size battery, but other sources of power can be easily substituted.

Figure 3:
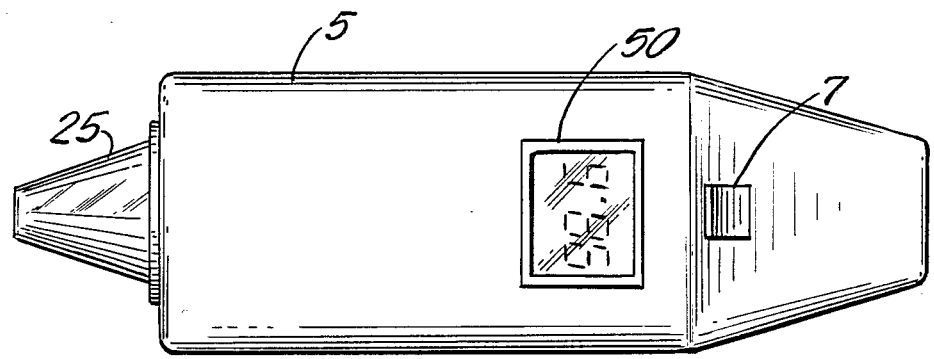
FIG. 3 is a top view of the apparatus of the present invention, and indicates the display and speculum location.

As mentioned above, PCB 35 is connected to display 50, which is external to housing 5. Referring to FIG. 3, display 50 is shown on the top of housing 5. Also shown are disposable speculum 25 and speculum release switch 7. Display 50 is preferably a liquid crystal display (LCD) since the LCD requires little power. LCD's perform best in brightly lit environments; obviously if the apparatus has expected duties in low-light areas, other displays such as light emitting diode displays (LED's) can be easily substituted. For most purposes, the LCD should suffice, and is connected to PCB 35 via conductive ribbon connector 51 (In FIG. 1). Control of the apparatus is made by switch 6 as connected by cable 70 to PCB 35.

Continuing with FIG. 1, it is seen that infrared radiation sensor assembly 10 partially extends outside housing 5 through opening 80, thus forming the portion of the apparatus that is directed toward the infrared radiation emissive target (e.g., ear drum). In this regard, disposable speculum 25 is used to cover the infrared radiation sensor assembly as it extends outside of housing 5. More particularly, disposable speculum 25 snugly fits onto housing 5 via frictional forces as translated through retaining nub 30. This snug fit is formed by depressing the cup shaped speculum over the housing opening. Speculum 25 is formed of an infrared radiation transparent material such as polyethylene or polypropylene which also are quite inexpensive. Removal of speculum 25 is accomplished by depressing switch 7. More particularly, switch 7 causes the extension of push rod 39 which in turn, causes the dislocation of the speculum from retaining nub 30. Spring 31 acts to retract push rod 39 and switch 7 into their unextended position in preparation for receipt of another disposable speculum. In addition to speculum disposal, it may be cost effective to provide speculums capable of recycle (after cleaning).

Figure 4:
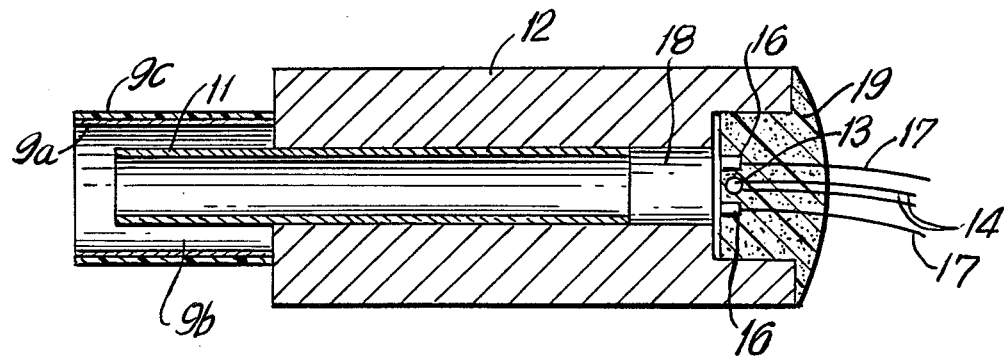
FIG. 4 is a detailed, longitudinal cross-section view of subassembly 10 from FIG. 1.

Referring now to FIG. 4, the infrared radiation sensor assembly is presented in detail. Wave guide 11 provides a uniform cylindrical tube with the open end extending outside housing 5 (as shown in FIG. 1 and discussed above), and the opposite end terminating at infrared radiation detector 18. The dimensions and orientation of wave guide 11 are such that the field of view of infrared radiation detector 18 is shaped to an angle of about six (6) degrees, so that the infrared radiation detector "sees" the infrared radiation emanating from the tympanic membrane (1 in FIG. 1) with little or no radiation from the ear canal. This insures that the apparatus measures the temperature of the tympanic membrane or, if not perfectly aimed, the average of the temperature of the tympanic membrane and the temperature of only that portion of the ear canal which is directly contiguous to the tympanic membrane and therefore very close in temperature to that of the tympanic membrane. The wave guide can be constructed of materials of relatively low infrared radiation emissivity with aluminum being preferred.

The infrared radiation detector 18 is preferably the thermopile type, which has become recognized in other industrial devices for infrared radiation detection. Thermopiles are equipped with plural reference (cold) junctions which, of course, are affected by ambient temperature. Plural detector posts, 16, are placed in close thermal contact with the reference junctions. Contact temperature sensor 13, such as a thermistor or thermocouple, is placed in close proximity to detector posts 16. The infrared radiation detector, detector posts 16, and thermistor 13 are bound together by an epoxy compound 19. Any means of binding the above components will be suitable if the components are combined in a manner that retains substantial isothermic conditions among the components, i.e., the detector, junctions, and thermistor are held at the same (ambient) temperature.

In addition, wave guide 11, and the above described detector assembly are also held in an isothermal state at ambient temperature by heat conducting block 12. To operate in this fashion, block 12 extends contiguously over a substantial portion of wave guide 11 and the detector assembly. Block 12 should be constructed of a good heat conductor, such as aluminum or copper with aluminum being preferred due to its lower infrared radiation emissivity. Block 12 should be of sufficient mass as to retain substantial isothermic conditions over the other components in infrared radiation sensor assembly 10. Cable 14 and 17 act to transmit the thermistor and infrared radiation detector signals respectively. Protective barrier 9a extends from block 12 concentrically around wave guide 11. Plastic cover 9c is contiguous to barrier 9a, with airspace 9b between 9a and wave guide 11.

The objective of the above-described relationship is to maintain isothermic conditions among the various components in the infrared radiation sensor assembly, even when ambient temperature changes. Since reference junctions are held at the same temperature of the components proximate thereto, these components now become infrared radiation "invisible" to infrared radiation detector 18. Furthermore, changes in ambient temperature will not affect the reading of the device, since ambient air temperature changes that result in a temperature change in the infrared radiation sensor assembly 10 are measured by thermistor 13, which thus provides a signal to compensate for the corresponding temperature shift. Finally, since infrared radiation sensor assembly 10 is thermally insulated from the environment via airspace 3 (See FIG. 2) the effect of sharp temperature transients in the external environment are substantially minimized, thereby increasing the temperature sensing accuracy of the device. This final point is especially important when measuring the temperature of the tympanic membrane since the device is placed proximate to the patient's body and subject to the heat excursions attendant thereto.

Figure 5:
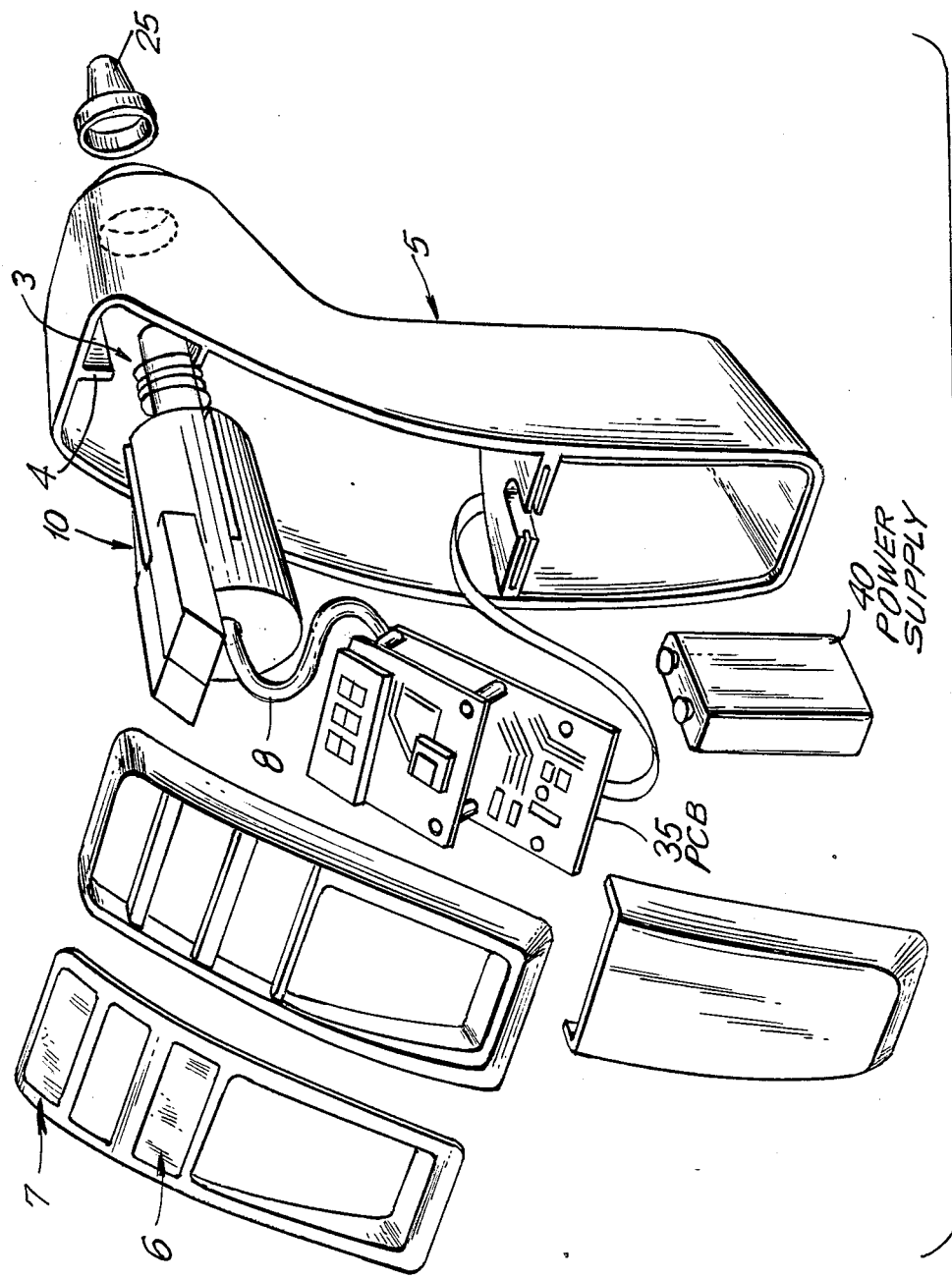
FIG. 5 is an assembly view of one particular arrangement of the present invention.

Referring now to FIG. 5, the outer housing is shaped in a manner that allows the operator's thumb to depress the sensor switch while the operator's fingers form a flush surface that is rested on the patient's cheek during the measurement process. This shape is important for two reasons. First, the procedure of using the invention apparatus will closely assimilate the per se well known use of otoscopes. Second, the geometry of the apparatus permits accurate alignment of the wave guide with the ear canal, thus enhancing signal accuracy.

The use of the temperature sensing apparatus is substantially enhanced by the above design considerations. The procedure is initiated by placing a fresh speculum onto the sensor device. The disposable speculum is shaped to fit into the ear canal opening in a fashion that directs the device toward the tympanic membrane, i.e., infrared radiation detector 18 and the tympanic membrane become opposed to each other and coupled by the combined de facto wave guide formed by the ear canal and wave guide 11. The user of the device merely positions the speculum lightly into the ear at an approximate perpendicular orientation. As discussed above, the proper orientation is easily attained, pursuant to the shape of the apparatus in conjunction with applying the procedure used with otoscopes. Once in position, the user depresses trigger switch 6 to obtain a temperature reading, usually in under two (2) seconds, and removes the device from the patient. The speculum is disposed of by depressing switch 7, dumping the speculum into a waste receptacle. The LCD display retains the measured tympanic temperature which can be recorded by per se well-known means. A new speculum is placed onto the device, which is now ready for the next measurement.

During the measurement interval in the above procedure, the infrared radiation detector is exposed to infrared radiation from the tympanic membrane, and generates an electrical signal corresponding to this infrared radiation exposure. Concurrently, thermistor 13 measures the real time temperature of the infrared radiation sensor assembly and generates a signal corresponding to this temperature. The infrared radiation signal is amplified, converted to temperature units and adjusted by the real time temperature of the infrared radiation sensor assembly vis-a-vis the thermistor signal. The resulting adjusted temperature signal is transmitted to display 50 providing the output from the device to the user.

It should be noted that the above descriptions are presented to illustrate the invention and that modifications by those skilled in the art are possible without departing from the spirit and scope of the invention.

What is claimed is:

1. An apparatus for measuring a temperature of an infrared radiation emissive target comprising: a housing having at least one infrared radiation receiving port; an infrared radiation sensor means enclosed in said housing and further comprising a wave guide means having one end accessible to infrared radiation, an infrared radiation detector means positioned to receive infrared radiation from said target as directed by said wave guide means, and further to generate a signal corresponding to a quantity of infrared radiation detected, a detector temperature sensor means positioned to measure a temperature of said infrared radiation detector means and further to generate a signal corresponding to said temperature of the infrared radiation detector means, said wave guide, and an isothermic block means, wherein said infrared radiation detector means and said detector temperature sensor means are held at or about an ambient temperature by said isothermic block means, a signal processing means for receiving said infrared radiation detector means signal and said detector temperature sensor means signal, and generating an output signal corresponding to the temperature of said infrared radiation emissive target.

2. The apparatus of claim 1, further comprising a portion of said housing adapted to receive and retain a power source means.

3. The apparatus of claim 1, wherein said wave guide means is a cylindrical tube with said infrared radiation accessible end positioned proximate to said infrared radiation receiving port in said housing.

4. The apparatus of claim 3, wherein said infrared detector means is a thermopile device positioned at a second, opposite end of said wave guide means.

5. The apparatus of claim 4, wherein said detector temperature sensor means is held in isothermic relationship with said reference junction, and further held at ambient temperature by said block means.

6. The apparatus of claim 3 wherein said isothermic block means further comprises a protective barrier substantially surrounding said infrared radiation accessible end of said cylindrical tube.

7. The apparatus of claim 6 wherein said protective barrier is spaced from said cylindrical tube.

8. The apparatus of claim 1, wherein said isothermic block means is a heat conducting material positioned proximate to said wave guide means and of sufficient mass to maintain substantially isothermic conditions between said wave guide means and said infrared radiation detector means.

9. The apparatus of claim 1, further comprising an insulation means positioned between said housing and said infrared radiation sensor means in a manner to inhibit heat transport between the housing and the infrared radiation sensor means.

10. The apparatus of claim 9, wherein said insulation means is an airspace between said housing and said infrared radiation sensor means formed by support studs extending between said housing and said infrared radiation sensor means.

11. The apparatus of claim 10, wherein a second airspace is formed between said infrared radiation sensor means and a speculum attachment adaptable to be positioned over said infrared radiation receiving port in said housing.

12. The apparatus as in claim 1 wherein said housing is shaped to conform to a human hand permitting said hand to rest on a patient's cheek in a manner that aligns said wave guide to said target during a temperature measurement procedure.

13. In combination in a device for the sensing of infrared radiation from a patient and determining patient body temperature based thereon, comprising: sensor means including an open-end wave guide having an inner end adjacent to a radiation detector means; an outer end of said sensor means being adapted for positioning adjacent to said patient to receive through an outer end of said wave guide radiation from the patient, said radiation is guided toward said radiation detector means by said wave guide for impingement thereon; a protective means formed to be essentially transparent to said radiation and adapted to be removably positioned over said outer end of the wave guide in a manner to limit sensor means contact with the patient; and heat conducting block means; wherein said radiation detector means and the wave guide are held at or about an isothermic condition by said heat conducting block means at or about a temperature corresponding to air temperature immediately adjacent to said heat conducting block means.

14. The device of claim 13, wherein said heat conducting block means is a cylindrical tube that fits over and is contiguous to a substantial portion of said wave guide, and further is of sufficient mass to substantially maintain said isothermic condition of said wave guide and radiation sensor.

15. The device of claim 14, wherein said insulation means comprises plural airspace regions.

16. The device of claim 15 wherein said heat conducting block comprises a protective barrier substantially surrounding said outer end of said sensor means.

17. The device of claim 16 wherein said protective barrier is spaced from said sensor means.

18. The device of claim 13, further comprising an insulation means positioned between the wave guide and an inner wall of said sensor means in a manner to reduce heat transfer therebetween.

19. The device of claim 13 wherein said housing is shaped to conform to a human hand permitting said hand to rest on a patient's cheek in a manner that aligns said wave guide to said subject during a temperature measurement procedure.

20. A method for measuring internal body temperature of a patient comprising the steps of:
 (a) Positioning a radiation sensor adjacent to an ear of the patient in a manner so that radiation emitted by a tympanic membrane of the ear is directed into said radiation sensor, and further said radiation is directed by an open ended wave guide means in said sensor onto a radiation detector means;
 (b) Converting said radiation impinging onto said radiation detector means into a signal that is dependent on a quantity of radiation received per unit time;

(c) Measuring a temperature of said radiation detector means and wave guide;
(d) Adjusting said radiation detector signal in response to said temperature of the radiation detector means and wave guide; and
(e) Displaying the tympanic membrane temperature as derived from said adjusted radiation signal wherein said radiation detector means and wave guide are substantially held at ambient temperature by an isothermal block means, and further steps b-d above are essentially concurrently performed.

21. The method of claim 20, wherein a thermistor is thermally coupled to said wave guide and radiation detector means to measure said temperature of the radiation detector means and wave guide.

* * * * *